United States Patent
Paule et al.

(10) Patent No.: US 11,318,177 B2
(45) Date of Patent: May 3, 2022

(54) ***LACTOBACILLUS FERMENTUM* FOR TREATING FRUCTOSE-RELATED DISEASES**

(71) Applicant: AIXSWISS B.V., Kerkrade (NL)

(72) Inventors: Jorg Paule, Hergenrath (BE); Fabio Oester, Dietikon (CH)

(73) Assignee: AIXSWISS B.V., Kerkrade (NL)

( * ) Notice: Subject to any disclaimer, the term of this patent is extended or adjusted under 35 U.S.C. 154(b) by 0 days.

(21) Appl. No.: 17/040,019

(22) PCT Filed: Mar. 12, 2019

(86) PCT No.: PCT/EP2019/056126
§ 371 (c)(1),
(2) Date: Sep. 21, 2020

(87) PCT Pub. No.: WO2019/179823
PCT Pub. Date: Sep. 26, 2019

(65) Prior Publication Data
US 2021/0015877 A1    Jan. 21, 2021

(30) Foreign Application Priority Data
Mar. 21, 2018 (EP) .................................... 18163018

(51) Int. Cl.
*A01N 63/00* (2020.01)
*A61K 35/747* (2015.01)
*A61P 1/00* (2006.01)
*A61K 9/00* (2006.01)

(52) U.S. Cl.
CPC .......... *A61K 35/747* (2013.01); *A61K 9/0053* (2013.01); *A61P 1/00* (2018.01)

(58) Field of Classification Search
CPC .................................................... A61K 35/747
See application file for complete search history.

(56) References Cited

U.S. PATENT DOCUMENTS

2010/0215738 A1*  8/2010  Ritter ................. A61P 43/00
                                                          424/456

FOREIGN PATENT DOCUMENTS

WO    WO 2015099617 A1    7/2015

OTHER PUBLICATIONS

Rivero-Gutierrez, Belen, et al., A synbiotic composed of Lactobacillus fermentum CECT5716 and FOS prevents the development of fatty acid liver and glycemic alterations in rats fed a high fructose diet associated with changes in the microbiota, Mol Nutr Food Res, vol. 61, No. 8, May 1, 2017.
International Search Report and Written Opinion for PCT/EP2019/056126, dated Jul. 9, 2019.
Zubiría Mg., et al., Deleterious Metabolic Effects of High Fructose Intake: The Preventive Effect of Lactobacillus kefiri Administration. Nutrients. May 17, 2017;9(5):470. doi: 10.3390/nu9050470. PMID: 28513533; PMCID: PMC5452200.

* cited by examiner

Primary Examiner — Albert M Navarro
Assistant Examiner — Mark Navarro
(74) Attorney, Agent, or Firm — Bryan D. Zerhusen, Esq.; Nicholas R. Herrel, Esq.; Cantor Colburn LLP

(57) ABSTRACT

The present invention is directed to a composition of *Lactobacillus fermentum* for use in the treatment of a fructose-related disease and a related method of treatment.

14 Claims, 11 Drawing Sheets

Figure 1:
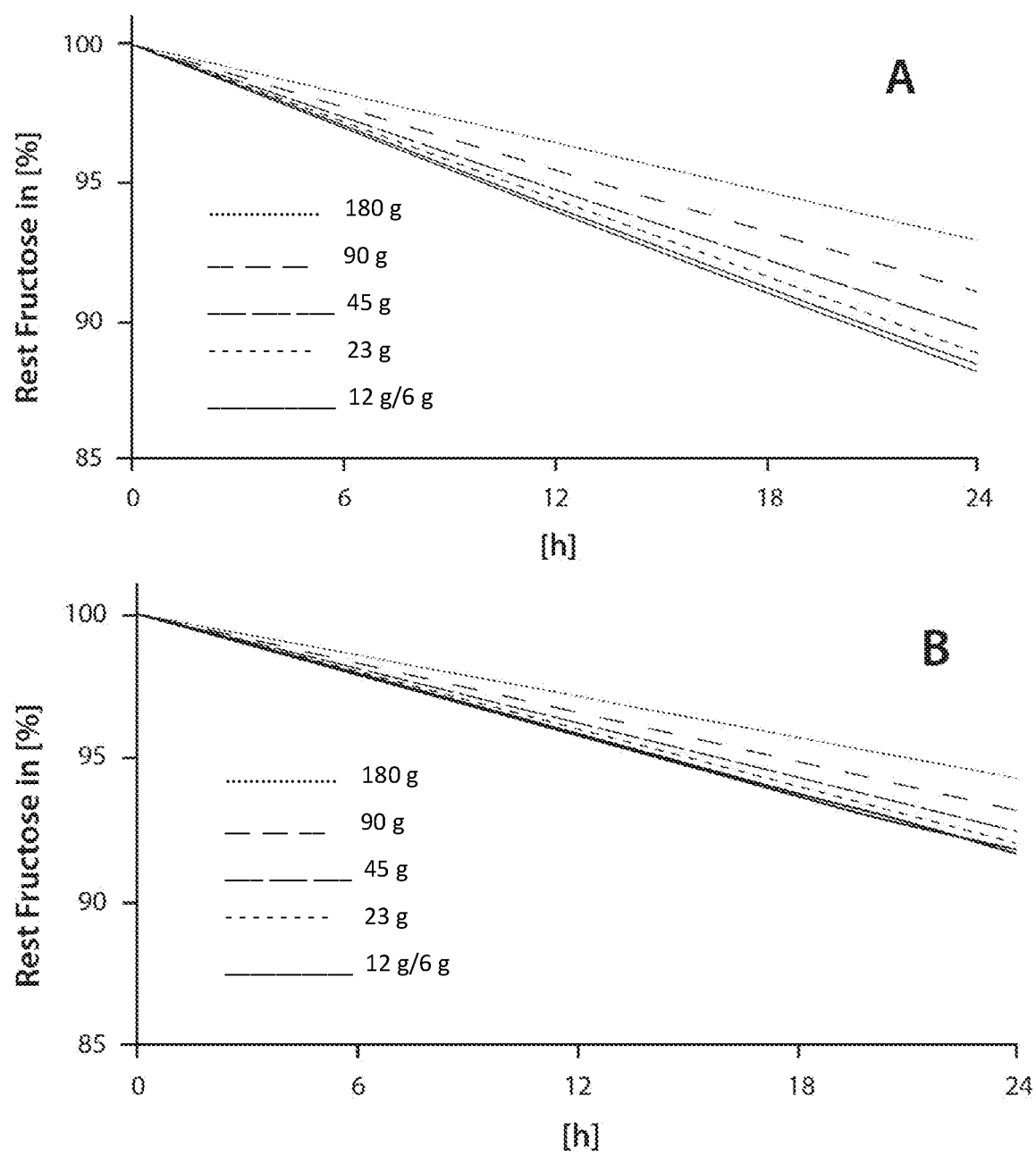

Fig. 2A    *Bifidobacterium breve*
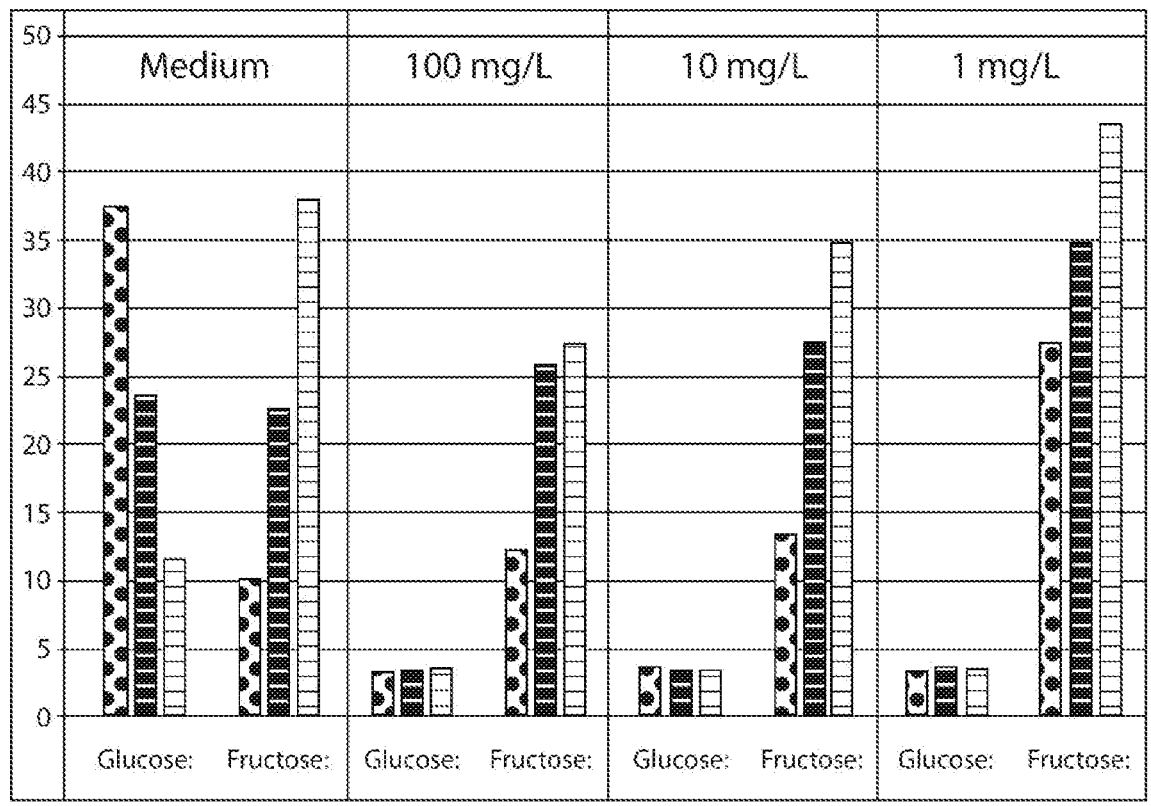
Fig. 2B    *Bifidobacterium infantis*
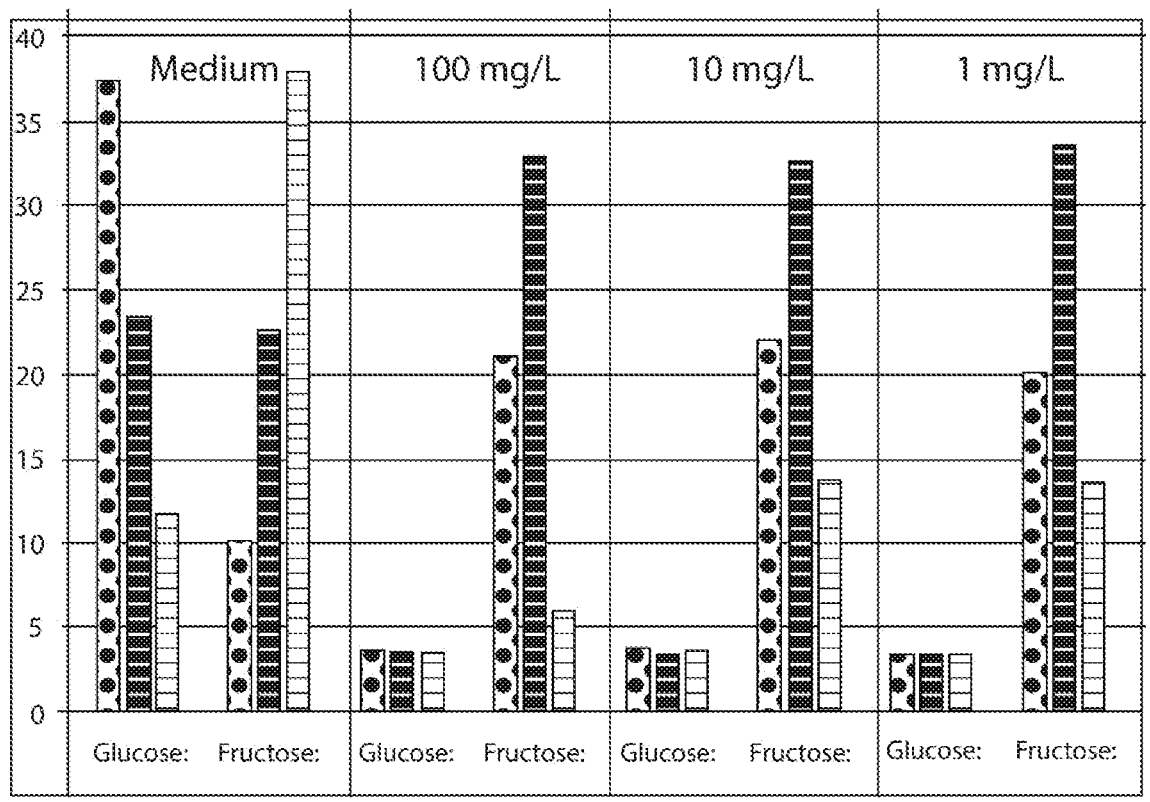

Fig. 2C  *Bifidobacterium lactis*
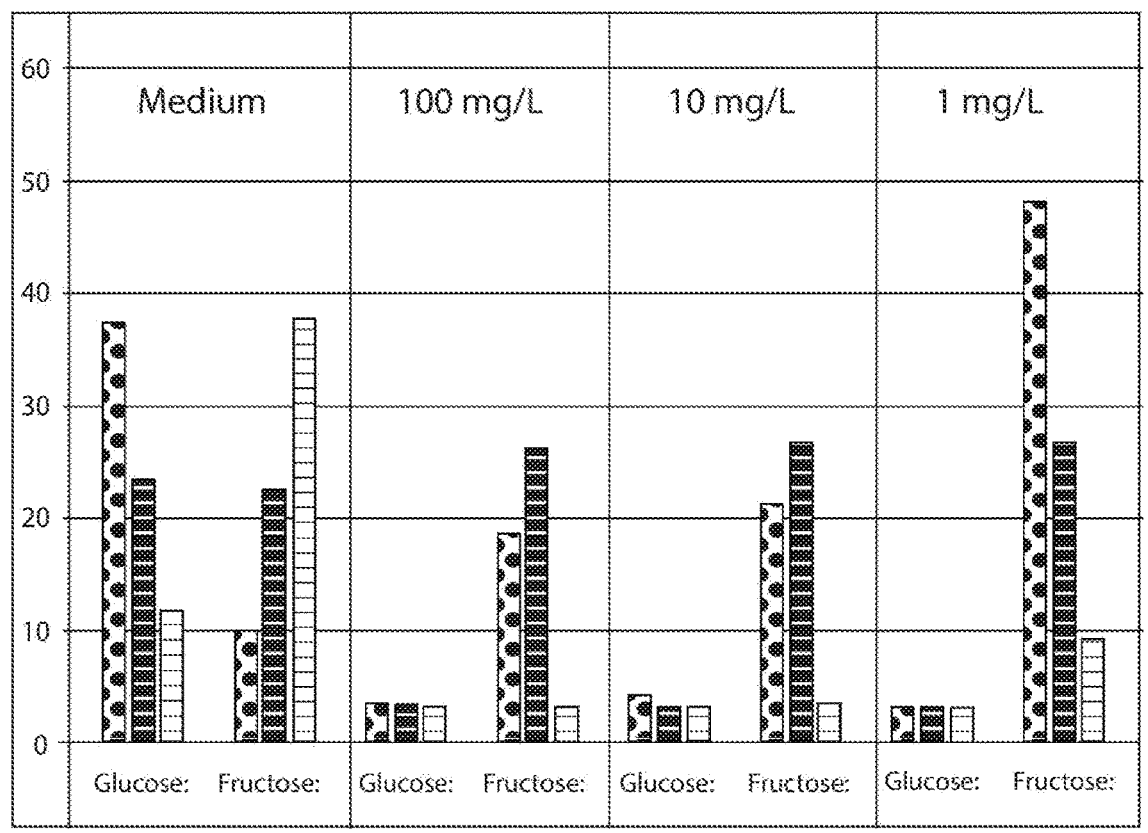
Fig. 2D  *Lactobacillus delbrueckii ssp. bulgaricus*
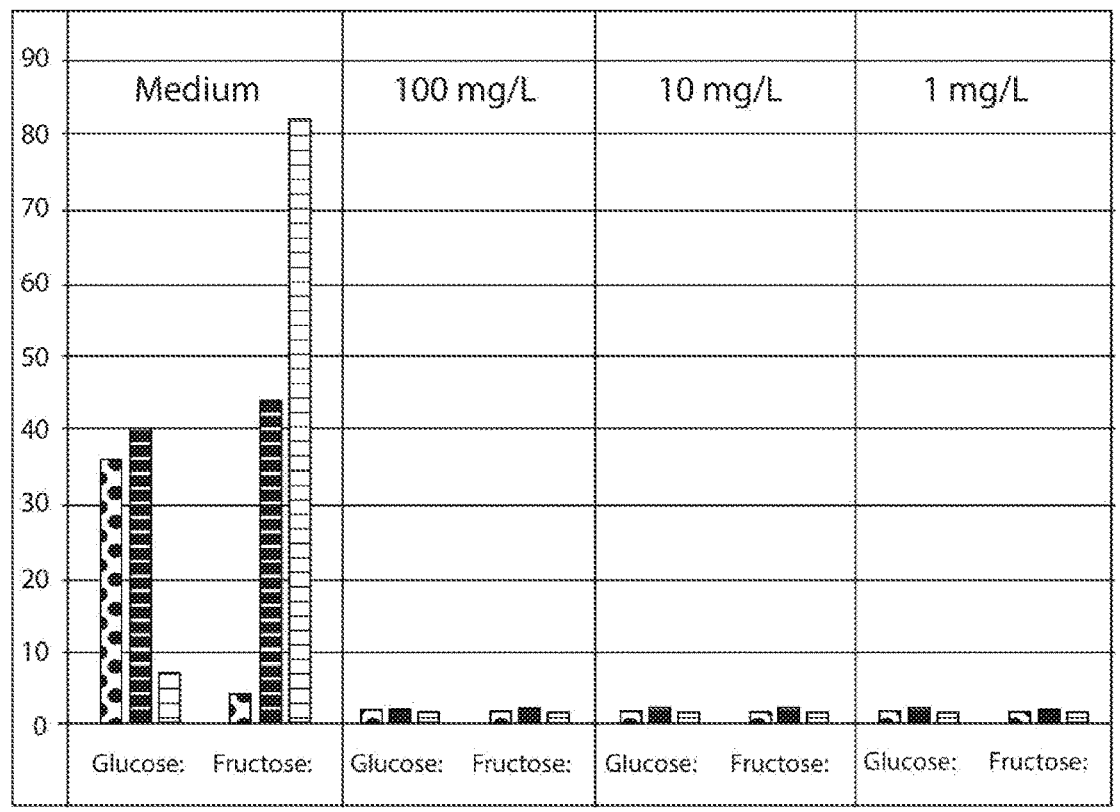

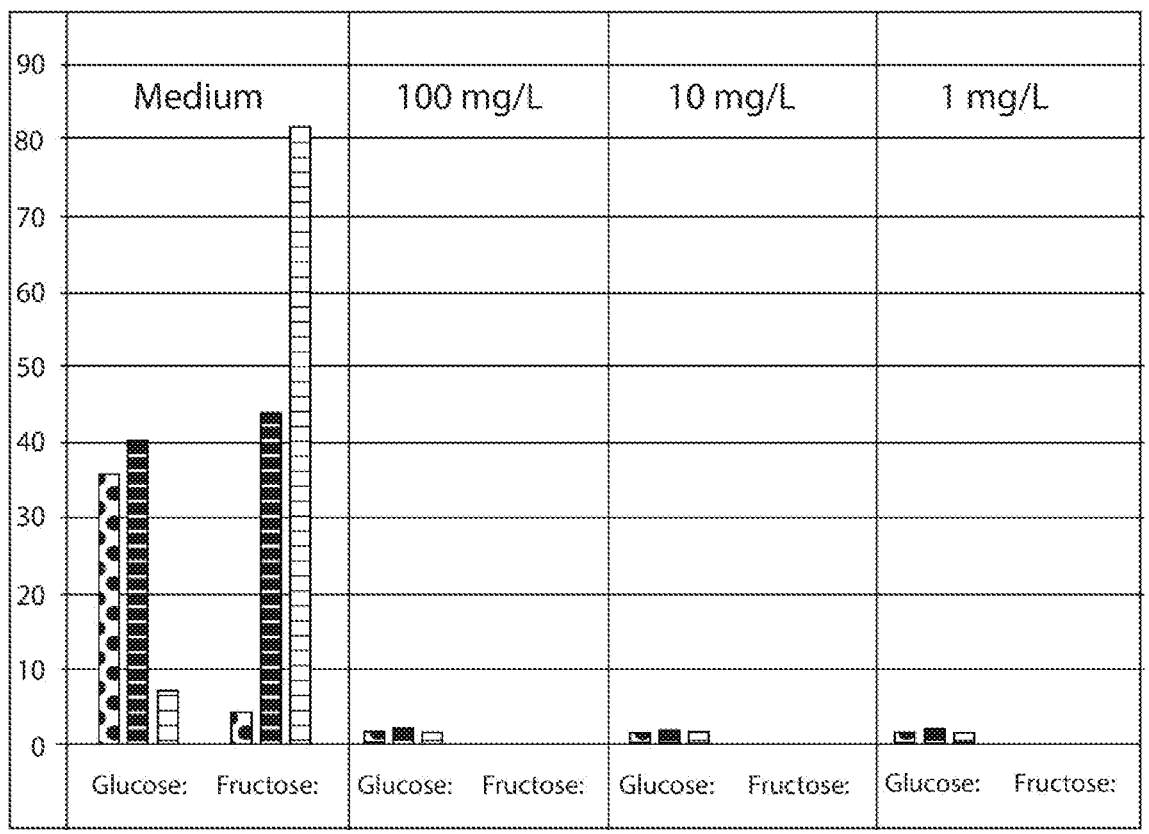
Fig. 2E *Lactobacillus fermentum*

LACTOBACILLUS FERMENTUM FOR TREATING FRUCTOSE-RELATED DISEASES

RELATED APPLICATIONS

This application is a National Stage of PCT/EP2019/056126, filed: 12 Mar. 2019, titled: *LACTOBACILLUS FERMENTUM* FOR TREATING FRUCTOSE-RELATED DISEASES, published as International Patent Application No. WO 2019/179823 A1, which claims the benefit and priority to European Patent Application No. 18163018.7, filed on 21 Mar. 2018, all of which are incorporated by reference in their entirety for all purposes.

The present invention is directed to a composition of *Lactobacillus fermentum* for use in the treatment of a fructose-related disease and a related method of treatment.

Fructose is a ketonic monosaccharide found in many plants and it constitutes one of three dietary monosaccharides, along with glucose and galactose, that are absorbed directly into the bloodstream during digestion. Natural sources of fructose are, e.g., honey, tree and vine fruits, flowers, berries and root vegetables. Fructose can be derived commercially from sugar cane, sugar beets and maize.

For the production of the abundantly used High-Fructose Corn Syrup (HFCS, a mixture of glucose and fructose as monosaccharides), corn starch is processed by glucose isomerase to convert glucose into fructose. Because fructose is a more potent sweetener than glucose, HFCS is often used as a preferred sweetener for foods and drinks. However, fructose is metabolized independent of insulin and when consuming fructose-sweetened foods or drinks, the feeling of satiety does not occur. Furthermore, large amounts of fructose enhance fat synthesis and it is believed that excessive fructose consumption is a cause of insulin resistance, obesity, elevated LDL cholesterol and triglycerides, leading to metabolic syndrome, type 2 diabetes and cardiovascular disease (Wikipedia on Fructose and Elliott S S et al. (2002) Am. J. Clin. Nutr. 76 (5): 911-22; Basciano H, et al. (2005) Nutrition & Metabolism. 2 (5): 5; Isganaitis E et al. (2005) Arterioscler. Thromb. Vasc. Biol. 25 (12): 2451-62; Malik et al. (2015) Journal of the American College of Cardiology. 66 (14): 1615-1624; Rippe, James M. et al. (2015) Advances in Nutrition (Bethesda, Md.). 6 (4): 430-439).

In addition to the above negative health effects, a small part of the population suffers from hereditary fructose intolerance, which is a severe (potentially fatal) disease caused by a lack of liver enzymes that break up fructose, and is currently treated by a strict diet.

A significant part of the population, namely about one third, suffers from fructose malabsorption (FM), also termed intestinal fructose intolerance or dietary fructose intolerance (DFI). FM is a digestive disorder in which absorption of fructose in the small intestine is impaired by deficient fructose carriers. When unabsorbed fructose passes into the large intestine, it can cause irritable bowel syndrome, diarrhea or pain. In some cases, FM can lead to decreased tryptophan, folic acid and zinc levels in the blood (Ledochowski M at al. (2001) Scand. J. Gastroenterol. 36 (4): 367-71; Ledochowski M et al. (1999) Clin. Chem. 45 (11): 2013-4).

Currently, two treatment options are available for FM. One being a fructose-deficient diet and the other is based on dietary supplements of xylose isomerase. However, the fructose-deficient diet can be difficult to adhere to and the ingestion of xylose isomerase is little effective as demonstrated in the experimental section below (Example 1 and FIGS. 1A-B), in which the commercial products Xylosolv (SCIOTEC Diagnostic Technologies GmbH, Austria), Fructozym (Biogena Naturprodukte GmbH & Co KG, Austria), Shandong-XI (Shandong Dianmei International Trade Co., Ltd., Shandong, China) and Sweetzyme IT (Novozymes A/S, Denmark) are analyzed. The main drawback of xylose isomerase-based agents is that the enzyme activity is too low to effectively reduce the fructose concentration. In the present experiments (Example 1), a reduction of 5 to 12% of the initial fructose load was extrapolated for the commercial enzymes Fructozym and Sweetzyme IT, which reduction is not sufficient for significantly reducing fructose concentrations or treating fructose intolerance or malabsorption. Furthermore, the xylose isomerase-catalyzed interconversion of fructose and glucose is an equilibrium reaction and xylose isomerase preferably catalyzes the conversion of glucose into fructose. Hence, the xylose isomerase-catalyzed conversion of fructose into glucose is only achieved under low glucose concentrations, which can even lead to the undesired result that fructose is produced instead of converted.

Another approach to reduce fructose levels in the intestinal system is based on the use of microorganisms that absorb and metabolize fructose. WO2015/099617 A1 ("WO '617) discloses and refers to strains of *Lactobacillus* in general and to two specific *Lactobacillus plantarum* strains ("KR6" deposited under DSM 27870 and a mutant thereof deposited under DSM 26329) for treating lactose malabsorption and intolerance, fructose malabsorption and intolerance, and bloating. WO '617 does not provide any experimental data on the utility of *Lactobacilli* in general but only discloses growth rates of different *Bifidobacteria* and *Lactobacilli* in media containing fructose, raffinose and/or lactose (Table 1 of WO '617); however, no experiments are available for media comprising a mixture of glucose and fructose for the organisms of Table 1. Also, three *Lactobacillus plantarum* strains (KR6, MP-10 and MP-2026) were tested for growth in media comprising a mixture of fructose, raffinose and lactose (Table 3 of WO '617) as well as in a media comprising a mixture of fructose, glucose, lactose and raffinose (Table 4 of WO '617). The latter experiment showed how much fructose was not consumed by the organisms and only *L. plantarum* KR6 was found to consume most of the available fructose while the other *L. plantarum* strains did not fully metabolize the fructose. Unfortunately, *L. plantarum* strains MP-10 and MP-2026 were not further characterized or defined in WO '617 and it is not clear whether and/or which of the *L. plantarum* strains is MP-10 or MP-2026 correspond(s) to DSM 26329. Also, WO '617 does not provide any data on the metabolic products that were produced by the *L. plantarum* strains and it therefore remains unclear whether any of these *L. plantarum* strains would be suitable for human or animal use.

In this context, yeast (e.g. *Saccharomyces cerevisiae* var. *boulardii*), *Bifidobacteria* (e.g. *B. breve, longum* and *animalis*) and *Lactobacilli* were investigated by the present inventors. However, these organisms revealed significant drawbacks caused by the products that they form upon metabolizing fructose or glucose. Yeast form ethanol (and carbon dioxide) as a product of sugar metabolism, and ethanol formation in the patient is undesirable because, e.g. the conversion of 24 g of sugar would already lead to 12 g of pure alcohol which is the WHO-recommended daily maximum for ethanol consumption in women. *Bifidobacteria* and *Lactobacilli* produce acetic acid and lactic acid at a ratio of 3:2. Lactic acid, in particular the D-(-)-isomer of lactic acid, can itself cause intolerances (lactose intolerance) and, more importantly, *Bifidobacteria* and *Lactobacilli* generally do not prefer fructose over glucose. In other words, in the presence of a mixture of glucose and fructose, the *Bifidobacteria* and *Lactobacilli* are generally known to metabolize glucose first which results in the accumulation of "undesired" fructose.

Further investigations of *Bifidobacteria* and *Lactobacilli* by the present inventors revealed that *Bifidobacterium infantis, B. breve, B. lactis* and *Lactobacillus delbrueckii* ssp. *bulgaricus* do not show a specific preference for fructose in the presence of glucose (see FIGS. 2A-D). In particular, the *Bifidobacteria* showed a significant preference for glucose. For *Lactobacilli* it is a generally accepted drawback that some strains, in particular the heterofermentors, can produce significant amounts acetic acid and ethanol when metabolizing sugars. Hence, many *Lactobacilli* are not suited for medical use because they also produce alcohol in undesired amounts when metabolizing sugars such as fructose or glucose.

It is the objective of the present invention to provide improved means for use in the treatment of fructose-related diseases, preferably for use in fructose malabsorption.

The above objective is solved by a composition comprising *Lactobacillus fermentum* for use in the treatment of a fructose-related disease.

It was surprisingly found that *L. fermentum* is a most effective strain for metabolizing fructose even in the presence of significant amounts of glucose. *L. fermentum* essentially meta-bolizes all of the fructose present in a 1:1 fructose/glucose mixture and leaves no significant or even measurable traces of fructose (see FIG. 2E). Because *L. fermentum* metabolizes essentially all the fructose in a sugar mixture, *L. fermentum* is suited for the treatment of fructose-related diseases such as fructose malabsorption but also for those forms of fructose-related diseases in which minimal concentrations of fructose in the intestinal system are dangerous such as hereditary fructose intolerance.

The term "fructose-related disease", as used herein, encompasses all diseases or disorders that are caused by the ingestion of fructose, e.g. hereditary fructose intolerance and fructose malabsorption.

In a preferred embodiment, the present invention is directed to a composition comprising *Lactobacillus fermentum* for use in the treatment of a fructose-related disease selected from the group consisting of hereditary fructose intolerance and fructose malabsorption, preferably fructose malabsorption. As noted above, fructose malabsorption is sometimes also referred to as "intestinal fructose intolerance" or "dietary fructose intolerance (DFI)", and these terms are considered meaning the same disease or condition as fructose malabsorption in the context of the present invention.

In a preferred embodiment, the *Lactobacillius fermentum* for use in the present invention is a *Lactobacillus fermentum* selected from the group consisting of LF2 (DSM 32733); LF3 (DSM 32734); LF4 (DSM 32735); LF5 (DSM 32736); LF6 (DSM 32737), and LF7 (DSM 32738).

It was surprisingly found that the above *Lactobacillus* strains exhibit particularly suitable properties for use in the treatment according to the present invention. For example, all of the above strains grow equally well in media comprising fructose, glucose or mixtures of fructose and glucose, i.e. they are capable of metabolizing fructose in the presence of varying amounts glucose. This finding is demonstrated in FIGS. 3A-F and 4 which show that the strains metabolize fructose and glucose at equally high rates and are therefore suitable for the use according to the present invention.

Figure 5A:
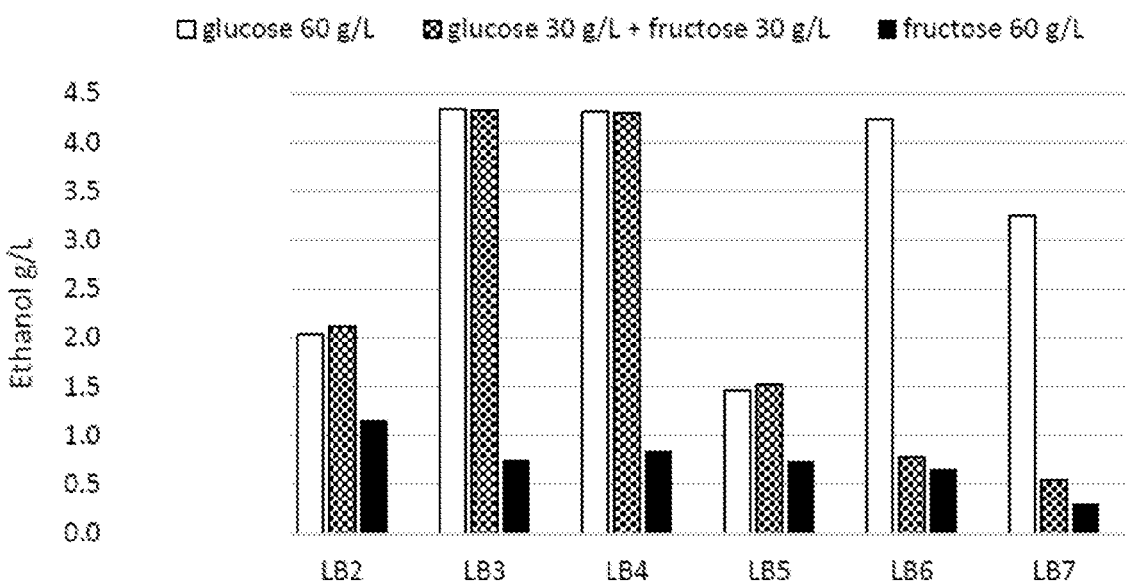
Figure 5B:
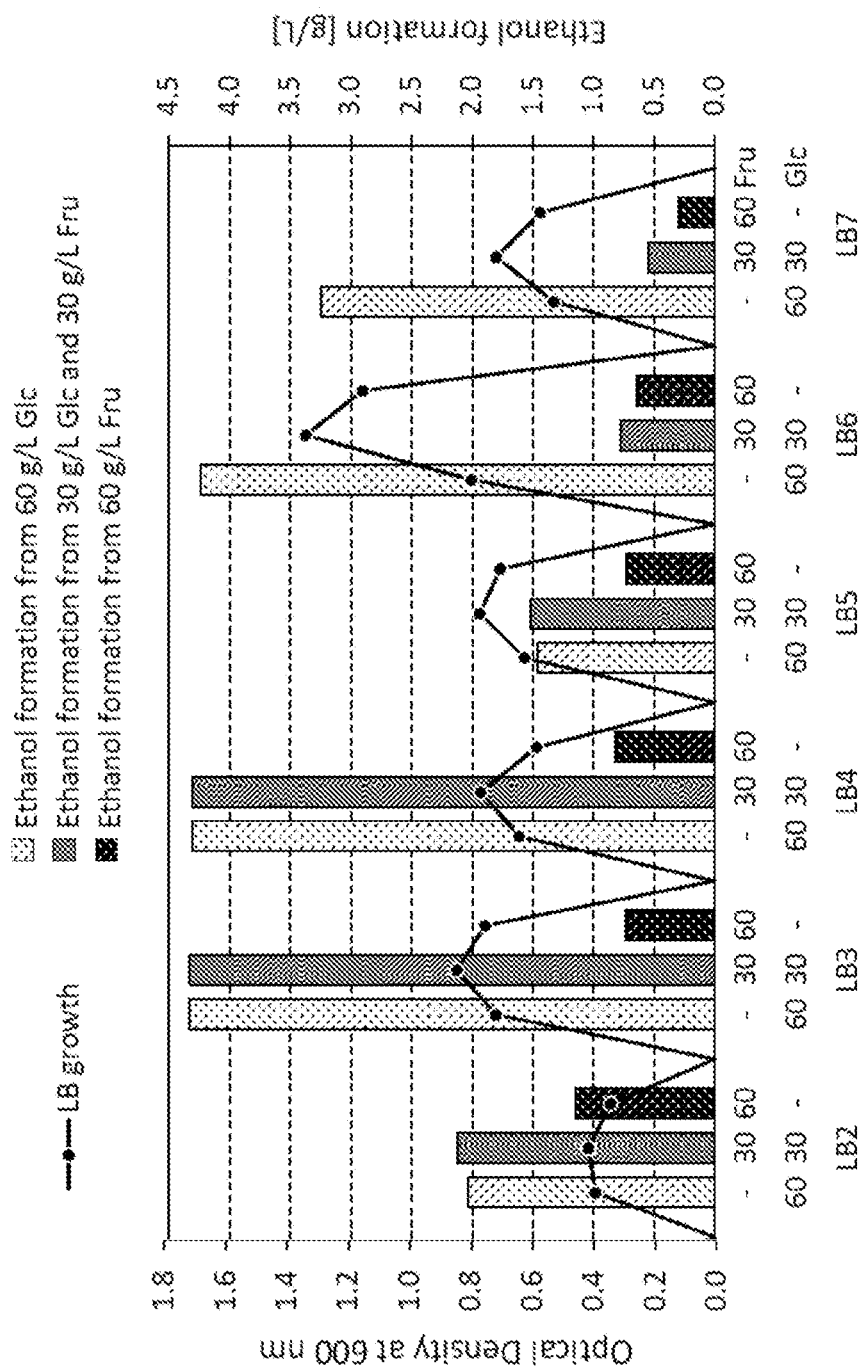

It was also demonstrated that the strains for use according to the present invention produce little undesired side products such as ethanol, in particular, when cultured with an excess of fructose (Example 4 and FIGS. 5A-B). Furthermore, FIG. 6 demonstrates that the strains are all viable and grow under pH conditions of between 6.6 and 7.4 and most of them up to a pH of 8 (Example 5). This pH range is especially suited for *Lactobacillus* growth in the intestinal tract of mammalians, in particular humans.

The preferred *L. fermentum* strains LF2, LF3, LF4, LF5, LF6 and LF7 were deposited under the terms of the Budapest Treaty on the International Recognition of the Deposit of Microorganisms for the purpose of Patent Procedure on 02.02.2018 at the Leibnitz-Institut DSMZ—Deutsche Sammlung von Mikroorganismen and Zellkulturen GmbH, Braunschweig, Germany by AixSuisse B. V., Eurode-Park 1-87, 6461KB Kerkrade, Netherlands under the following accession numbers: LF2 (DSM 32733), LF3 (DSM 32734), LF4 (DSM 32735), LF5 (DSM 32736), LF6 (DSM 32737), and LF7 (DSM 32738). Suitable growth media and conditions for *L. fermentum* and the *L. fermentum* strains LF2 to LF7 are provided in the Examples 2, 3 and 5 below.

The composition comprising *L. fermentum* and/or any of the above *Lactobacillus fermentum* strains can be any composition that is suitable for administering a viable and bioavailable form of *L. fermentum* or the above *L. fermentum* strains to a subject to be treated, preferably to a human or animal. In other words, the composition of *L. fermentum* or the above *L. fermentum* strains must comprise the *L. fermentum* or the above *L. fermentum* strains in a form that allows the bacterium to metabolize sugars, in particular fructose, in the subject to be treated and/or preferably proliferate and/or preferably grow upon administration to the subject to be treated.

Suitable compositions for use in the present invention are, e.g., pharmaceutical compositions such as tablets, capsules, powders, freeze-dried powders, liquid preparations, syrups, or additives in food or feed that contain a pharmaceutically effective amount of *L. fermentum* or the above *L. fermentum* strains together with adequate amounts of pharmaceutically or veterinary acceptable excipients and/or diluents.

Pharmaceutically or veterinary acceptable excipients include excipients that modulate the pH of the environment for improved fructose metabolizing efficacy of the *L. fermentum* or the above *L. fermentum* strains for use according to the present invention. Examples for such excipients include, e.g., polyvinyl acetate phthalate (PVAP), hydroxypropyl methylcellulose phthalate (HPMCP), cellulose acetate trimellate, cellulose acetate phthalate (CAP), hydroxypropyl methyl-cellulose phthalate 50 or 55, Eudragit L 100-55, L-30D, L 100, FS 30D or S100.

While oral administration of the above composition is preferred, the composition of the present invention can also be administered rectally, topically, enterally or as an injection.

In a further aspect, the present invention is directed to a human food or animal feed composition comprising *Lactobacillus fermentum*, preferably *Lactobacillus fermentum* selected from the group consisting of LF2 (DSM 32733), LF3 (DSM 32734), LF4 (DSM 32735), LF5 (DSM 32736), LF6 (DSM 32737), and LF7 (DSM 32738) for use in the treatment of a fructose-related disease.

In a preferred embodiment, the present invention is directed to a human food or animal feed composition for use according to the present invention, wherein the fructose-related disease is a fructose-related disease selected from the group consisting of hereditary fructose intolerance and fructose malabsorption, preferably fructose malabsorption.

The composition, food or feed for use according to the present invention may be a probiotic composition and optionally further comprise other probiotic strains. For example, the probiotic composition may confer a beneficial impact on, e.g., the regulation of gut microbiota, the immune system. It is preferred that the probiotic is capable of adhesion to the intestinal epithelium and can thus be present in the gut for a longer period of time.

Suitable amounts of *L. fermentum* or of the above *L. fermentum* strains in the composition, food or feed of the present invention for administration to a subject to be treated vary and are not limited to specific amounts as long as the amount is effective for use according to the present invention, in particular effective for the reduction of fructose concentrations in the intestine of a subject to be treated.

It is preferred that the composition, pharmaceutical composition, food or feed described above comprises *L. fermentum* or at least one of the above *L. fermentum* strains for use according to the present invention so that the amount of *L. fermentum* or of the at least one of the strains that is available for the subject to be treated is about $10^3$-$10^{14}$ CFU per day, preferably $10^6$-$10^{13}$ CFU per day, more preferably $10^8$-$10^{12}$ CFU per day, most preferably $10^9$-$10^{11}$ CFU per day. These amounts depend, inter alia, on the weight of the subject to be treated and is preferably about $10^9$-$10^{12}$ CFU per day for humans and $10^7$-$10^{10}$ CFU per day for animals. It is preferred that *L. fermentum* or one or more of the above *L. fermentum* strains is administered at a dose of at least $10^3$-$10^{14}$ CFU per day, preferably $10^6$-$10^{13}$ CFU per day, more preferably $10^8$-$10^{12}$ CFU per day, most preferably $10^9$-$10^{11}$ CFU per day to the subject to be treated.

The skilled person understands that the specific amount of *L. fermentum* or of the above *L. fermentum* strains for the subject to be treated depends on a variety of factors, such as the activity of the specific strain, the age, body weight, sex, diet, time of administration, route of administration, rate of excretion, drug combination and the severity of the disease or condition to be treated.

In a preferred exemplary embodiment, the composition for use in the present invention comprises *L. fermentum* in a concentration for daily dosage forms providing an amount of about $10^3$-$10^{14}$ CFU *L. fermentum* per day, preferably $10^6$-$10^{13}$ CFU per day, more preferably $10^8$-$10^{12}$ CFU per day, most preferably $10^9$-$10^{11}$ CFU per day.

Another aspect of the present invention is directed to a method for the therapeutic or prophylactic treatment of a fructose-related disease, preferably a fructose-related disease selected from the group consisting of hereditary fructose intolerance and fructose malabsorption, more preferably fructose malabsorption, comprising the steps of:

(a) providing a composition comprising *Lactobacillus fermentum*; and (b) administering the composition of (a) to the subject in need thereof in a pharmaceutically effective amount, preferably by oral administration.

Preferably, the subject for treatment is selected from the group consisting of a human and an animal, preferably a human and mammal, more preferably a human.

In a preferred embodiment, the method of treatment is one, wherein the composition comprises a *Lactobacillus fermentum* selected from the group consisting of LF2 (DSM 32733), LF3 (DSM 32734), LF4 (DSM 32735), LF5 (DSM 32736), LF6 (DSM 32737), and LF7 (DSM 32738).

In a further preferred embodiment, the method of treatment is one, wherein the composition is administered in an amount of about $10^3$-$10^{14}$ CFU *L. fermentum* per day, preferably $10^6$-$10^{13}$ CFU per day, more preferably $10^8$-$10^{12}$ CFU per day, most preferably $10^9$-$10^{11}$ CFU per day.

If no other indication is given, the reference to *L. fermentum* in the present invention also includes the *L. fermentum* strains LF2 (DSM 32733), LF3 (DSM 32734), LF4 (DSM 32735), LF5 (DSM 32736), LF6 (DSM 32737), and LF7 (DSM 32738).

The invention has been described generally and also with emphasis upon preferred embodiments and will be further illustrated by the following examples, none of which should be construed to limit the scope of the invention beyond the scope of the appended claims.

FIGURES

FIG. 1 shows the calculated effects of one daily dose of Fructozym (FIG. 1A, three capsules of 30 mg) and Sweetzyme IT (FIG. 1B, 300 mg granulate). The graphs show the expected percentage of fructose degradation in the intestine with a load of 180 g, 90 g, 45 g, 23 g, 12 g and 6 (top to bottom in each FIGS. 1A and 1B) of fructose over a period of 24 h. In any case, less than 12% of the fructose load was degraded by the isomerase enzyme.

FIGS. 2A-E depicts a comparison of the sugar metabolism of 5 different organisms. On each figure, the y-axis indicates the sugar concentration in mM after 20 h incubation with the organisms at 37° C. The x-axis denotes different media compositions and different organism concentrations (100 mg/L, 10 mg/L and 1 mg/L organism concentration). Each set of three bars depicts the measured amount of either glucose or fructose and each individual bar represents a medium comprising either glucose (dotted bar), glucose and fructose (solid black with white stripes) or only fructose (while with black stripes) from left to right. FIG. 2A shows the results for *Bifidobacterium breve*, FIG. 2B for *Bifidobacterium infantis*, FIG. 2C for *Bifidobacterium lactis*, FIG. 2D for *Lactobacillus delbrueckii* ssp. *bulgaricus* and FIG. 2E for *Lactobacillus fermentum*. Clearly, only *L. fermentum* was able to metabolize all fructose in the presence of glucose.

Figure 3A:
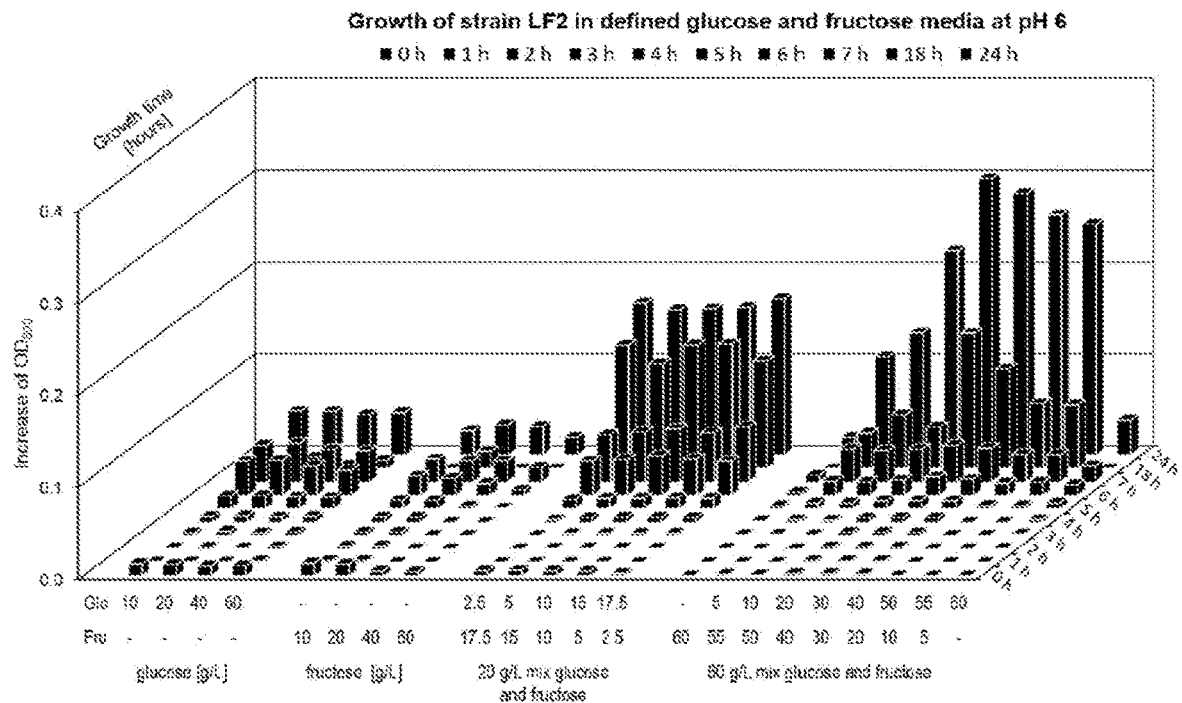
Figure 3B:
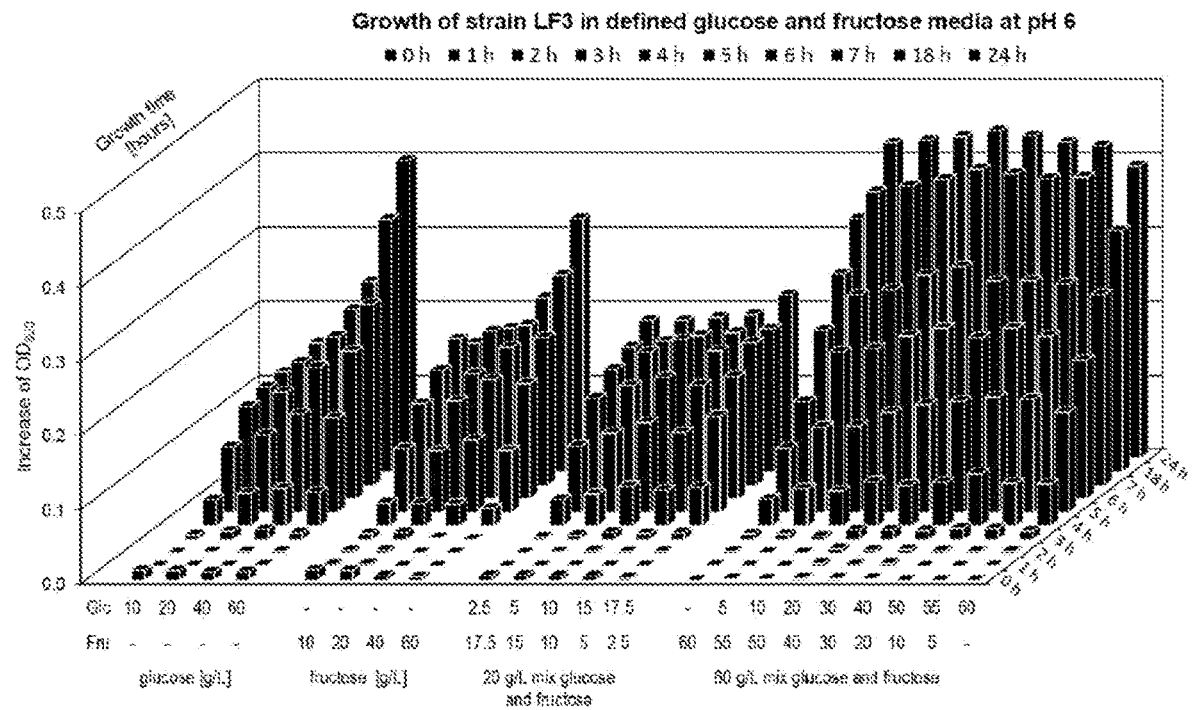
Figure 3C:
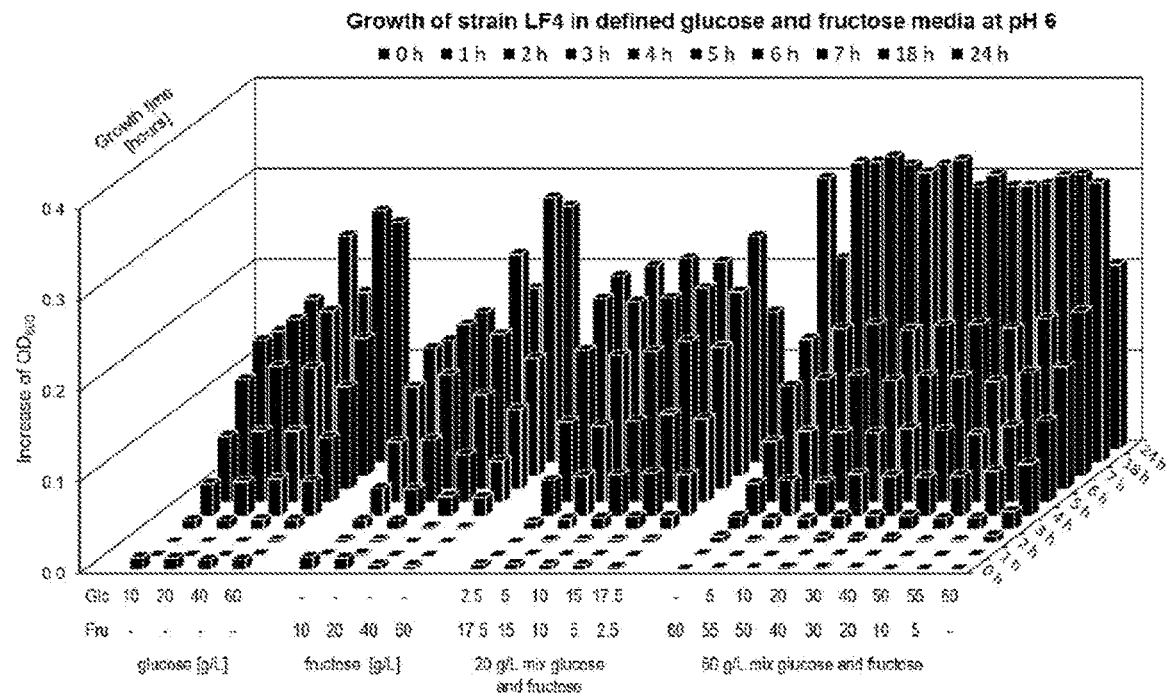
Figure 3D:
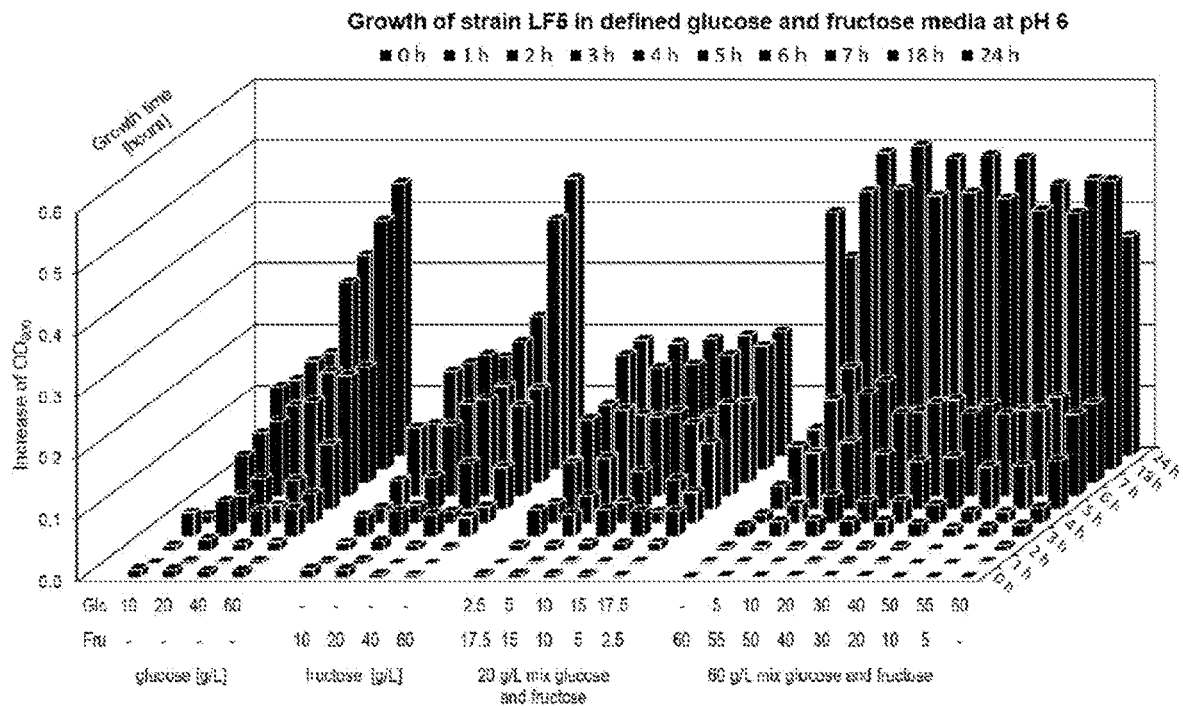
Figure 3E:
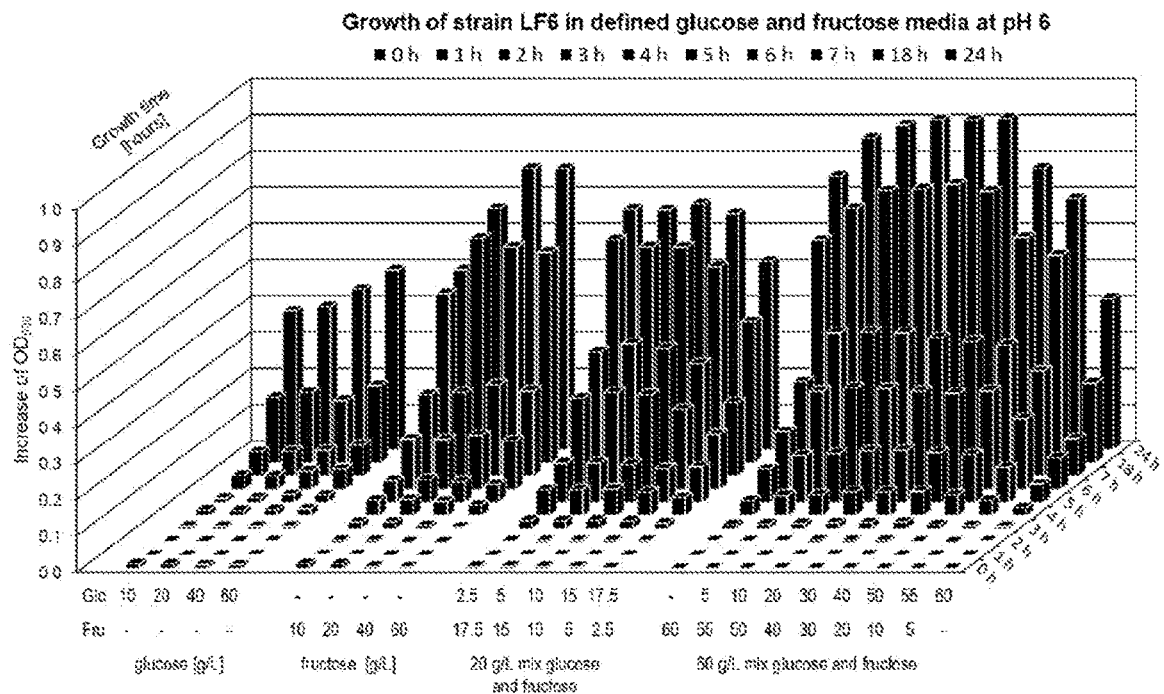
Figure 3F:
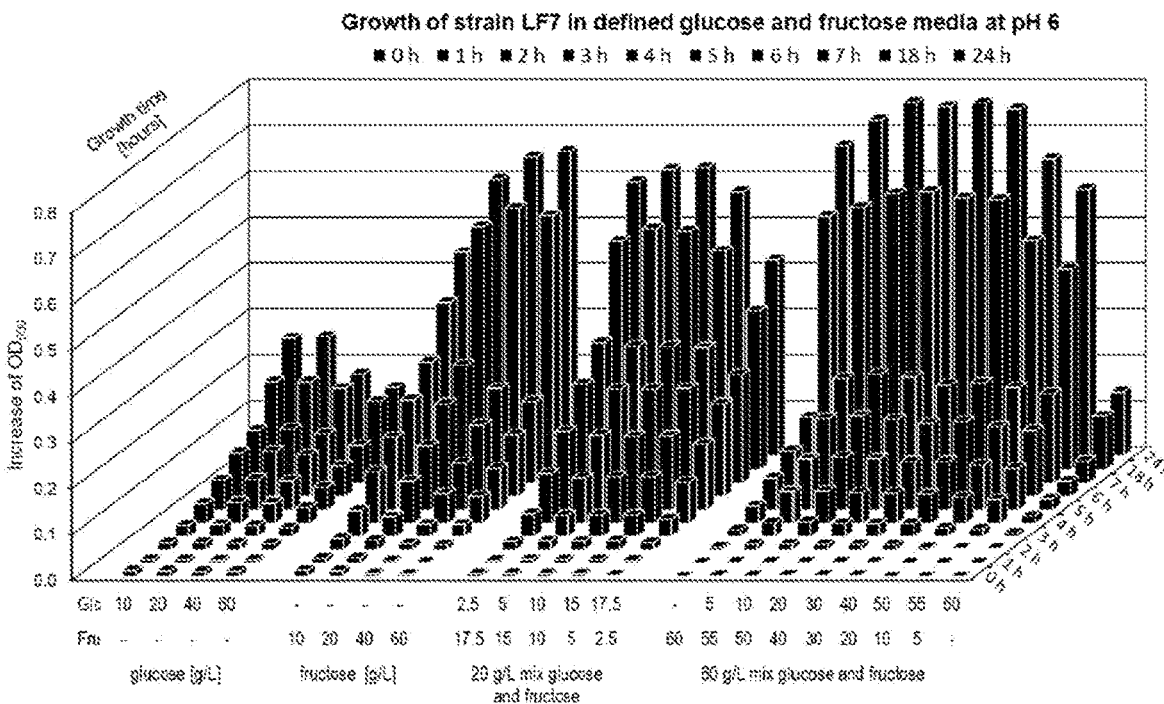

FIGS. 3A-F show growth rates (optical density) of the preferred *L. fermentum* strains for use according to the present invention in different media comprising either glucose, fructose or different mixtures of fructose and glucose. The y-axis notes the optical density of the solution, the x-axis shows different media compositions and the z-axis denotes the time of growth. All strains grow equally well and at equal rates in media comprising fructose, glucose or mixtures thereof. This finding demonstrates that the strains metabolize fructose and glucose at equally high rates and are therefore suitable for the use according to the present invention. FIG. 3A shows the result for LF2 (DSM 32733), FIG. 3B for LF3 (DSM 32734), FIG. 3C for LF4 (DSM 32735), FIG. 3D for LF5 (DSM 32736), FIG. 3E for LF6 (DSM 32737) and FIG. 3F for LF7 (DSM 32738).

Figure 4:
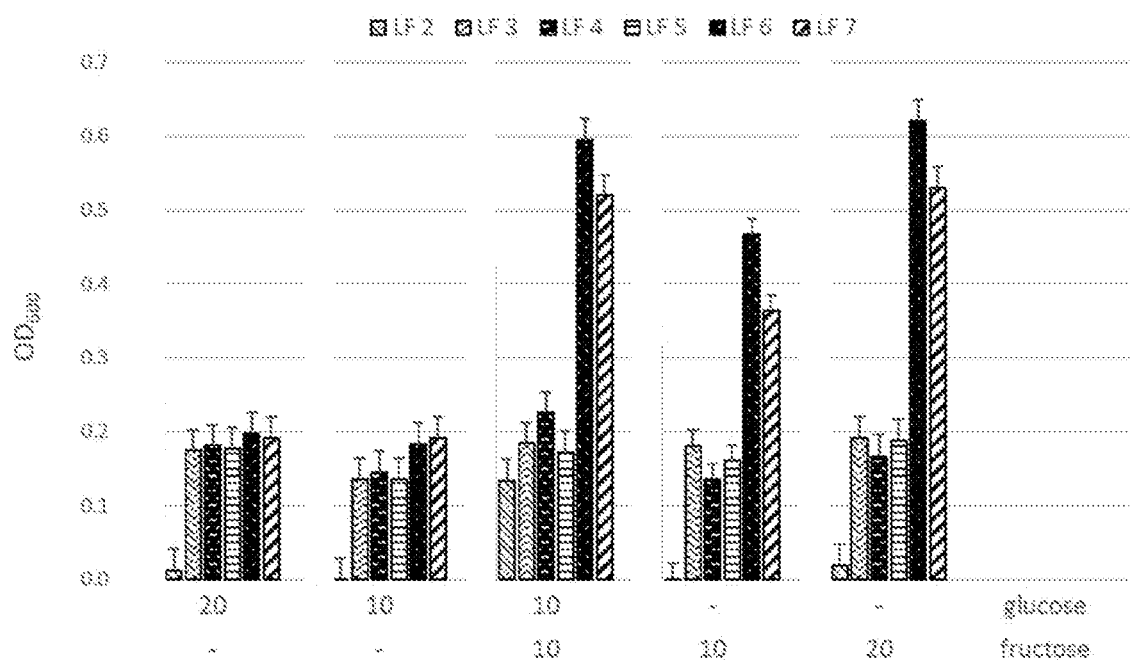

FIG. 4 summarizes the growth (optical density) of the strains for use according to the invention in media comprising glucose, fructose and mixtures thereof. All strains are suited for metabolizing fructose in the presence of glucose.

FIGS. 5A-B show how much ethanol is produced by the strains for use according to the present invention when cultured in media comprising glucose, fructose or mixtures thereof. Importantly, all strains produce minimal amounts of ethanol when cultured with an excess of fructose (LB2-7 correspond to LF2-7).

Figure 6:
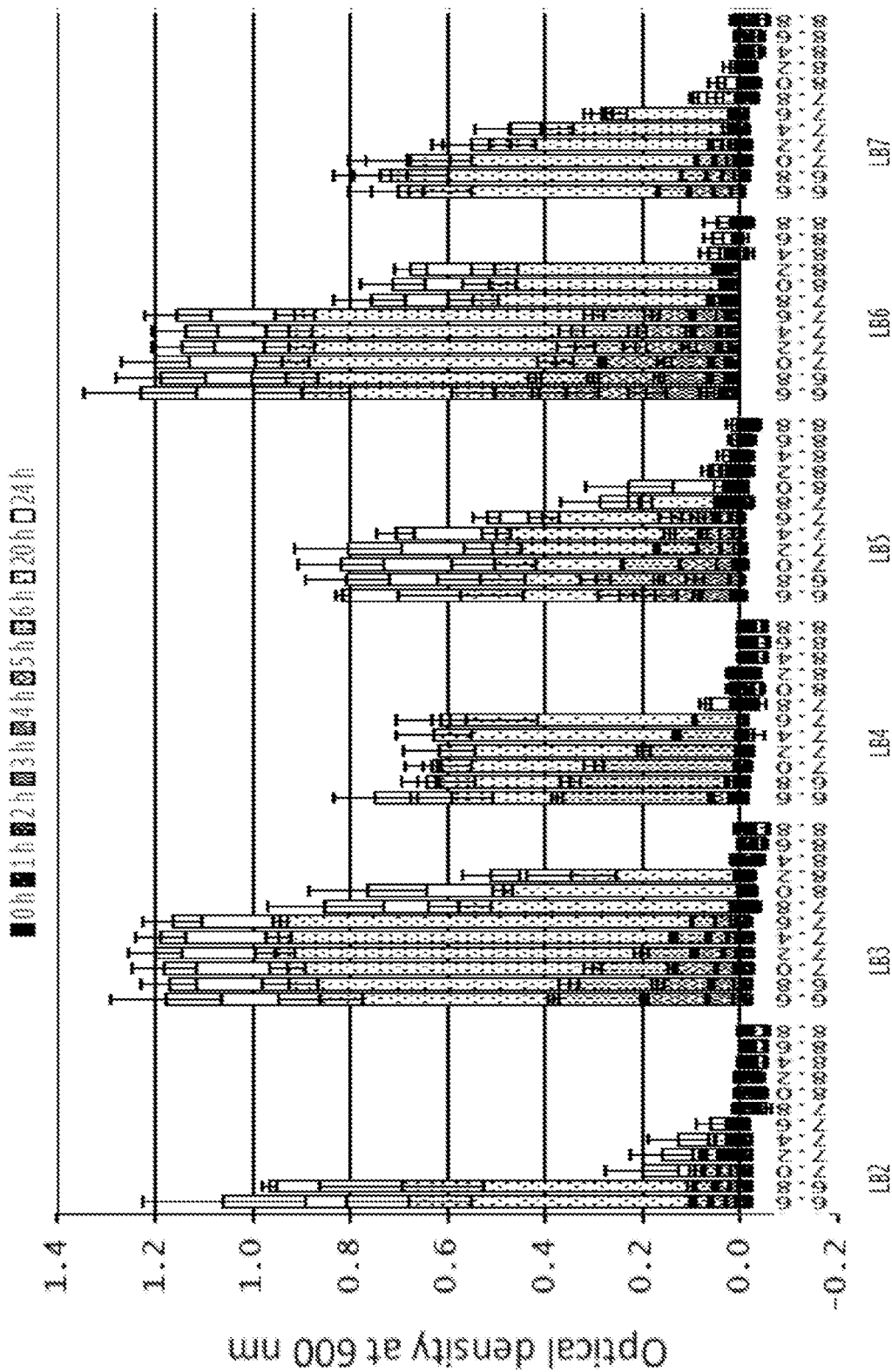

FIG. 6 characterizes the pH sensitivity of the strains for use according to the present invention (see Example 5). All strains were able to grow under pH conditions of between 6.6 and 7.4 and most of them up to a pH of 8 (the term "LB" as depicted in FIG. 6 refers to the same strains named "LF").

Figure 7:
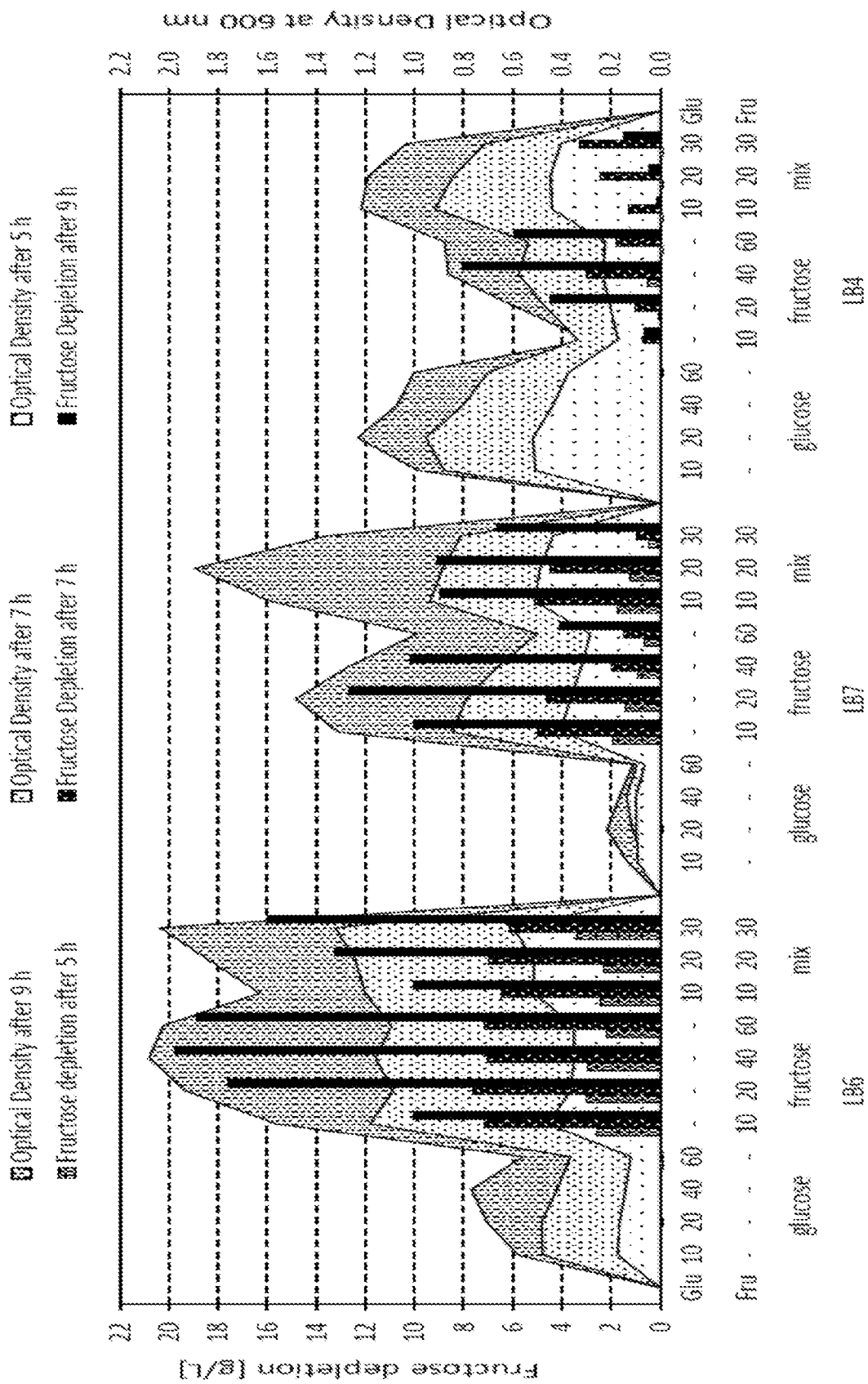

FIG. 7 depicts Fructose utilization of *Lactobacillus fermentum* strains LF4, LF6 and LF7 in defined sugar media.

EXAMPLES

Example 1: Xylose Isomerase Activity on Fructose Conversion

Glucose concentrations were measured using a standard hexokinase/glucose-6-phosphate-dehydrogenase assay and all samples for measurement were diluted to concentrations of less than 300 µM [fructose+glucose]. Samples of 100 mg Shandong-XI (Shandong Dianmei International Trade Co., Ltd., Shandong, China) and Sweetzyme IT (Novozymes A/S, Denmark) each, 30 mg capsules of Fructozym (Biogena Naturprodukte GmbH & Co KG, Austria) and Xylosolv (SCIOTEC Diagnostic Technologies GmbH, Austria) were suspended in 10 mL PBS and shaken for 1 h at 37° C. The samples were centrifuged. The pellets were suspended in PBS, centrifuged and after discarding the supernatant, the pellets were incubated in 10 mL of a fresh Tris-HCl buffer, pH 8, 30 mM magnesium chloride and 1.25 M fructose at 37° C. 1 mL of the supernatant obtained after the first centrifugation was mixed with 9 mL of the same buffer and incubated at 37° C. Xylosolv and Fructozym showed activities in of 188 mU/mg and 156 mU/mg. Sweetzyme IT showed little activity of the pellet (68 mU/mg after 1 h decreasing to 54 mU/mg after 16 h). Shandong-XI did not have any xylose isomerase activity. For time-correlated measurements, Shandong-XI and Sweetzyme IT (50 mg each) and one 30 mg capsule each of Fructozym and Xylosolv was suspended in 10 mL Tris-HCl buffer, pH 8, 30 mM magnesium chloride and 1.25 M fructose at 37° C. for 1 h and the glucose concentration was monitored for 4 h. Again, Shandong-XI did not show any activity and Sweetzyme IT showed a slightly higher activity (124 mU/mg). Fructozym showed a lower activity than before (31 mU/mg) and Xylosolv showed a higher activity than before (139 mU/mg).

For a simulation of fructose reduction in the intestine (FIG. 1A-B), it was assumed that 6 to 180 g of fructose are consumed with food which are then present in 3 L of intestinal fluid. Using this concentration, it can be calculated that 0.7/0.5 g glucose are converted from a load of 6 g of fructose (12.8/10.2 g for 180 g) by Fructozym (three capsules of 30 mg isomerase)/Sweetzyme IT (300 mg granulate), respectively. This amounts to a reduction of 5 to 12% of the initial fructose load and is not suitable for significantly reducing fructose concentrations or treating fructose intolerance or malabsorption.

Example 2: Comparison of Glucose and Fructose Metabolism of *Bifidobacteria* and *Lactobacilli*

For the measurement of fructose metabolism in the comparison of bifidobacteria (see FIGS. 2A-C), a medium of the following composition was prepared anaerobically, then autoclaved and used for cultivation at 37° C.: trypsin digestion of milk protein (casein) 10 g/L, yeast extract 5 g/L, meat extract 5 g/L, tryptic digestion of soy protein 5 g/L, di-potassium hydrogen phosphate 2 g/L, calcium chloride 10 mg/L, manganese chloride 50 mg/L, Tween 80 1 g/L, NaCl 5 g/L, sodium carbonate 400 mg/L, cysteine 500 mg/L, resazurin (25 mg/100 mL) 4 mL/L. 10 g of sugar (glucose, fructose or a 1:1 mixture of both (5 g+5 g)) was added to the medium.

For the measurement of fructose metabolism in the comparison of *lactobacilli* (see FIGS. 2D-E), a medium of the following composition was prepared anaerobically, then autoclaved and used for cultivation at 37° C.: trypsin digestion of milk protein (casein) 10 g/L, yeast extract 5 g/L, meat extract 10 g/L, Tween 80 1 g/L, di-potassium hydrogen phosphate 2 g/L, sodium acetate 5 g/L, ammonium citrate 2 g/L, magnesium sulfate 200 mg/L, manganese chloride 50 mg/L, cysteine 500 mg/L, resazurin (25 mg/100 mL) 4 mL/L. To this medium, either 10 g/L glucose, 10 g glucose and 10 g fructose, or 20 g fructose was added.

The colony count was carried out in the liquid medium. For evaluating the sugar metabolism, 100 mg/L, 10 mg/L and 1 mg/L of the samples and the remaining sugar content was determined after 20 h at 37° C. by centrifuging the cells off, diluting the medium 1:10 and determining the glucose concentration by the following optical-enzymatic test. Glucose was converted to glucose-6-phosphate with hexokinase and ATP and glucose-6-phosphate was oxidized with glucose-6-phosphate dehydrogenase and $NADP^+$ to obtain 6-phosphogluconolactone. The NADPH that is formed during this reaction can be quantified at 365 nm and this result was used to determine the glucose concentration ($\varepsilon$=3.4 $mM^{-1}$ $cm^{-1}$). By adding glucose-6-phosphate isomerase, the fructose concentration could also be determined.

The CFU/g of all samples was then determined:
*Bifidobacterium breve:* $1.0*10^{11}$ CFU/g in glucose medium, $3.5*10^{11}$ CFU/g in mixed medium (Glc and Fru) and $1.2*10^{12}$ CFU/g in fructose medium; average: $5.6*10^{11}$ CFU/g.
*Bifidobacterium infantis:* independent of the sugar: $1.0*10^{11}$ CFU/g.
*Bifidobacterium lactis:* $1.0*10^{11}$ CFU/g in media with glucose or fructose only, $3.0*10^{11}$ CFU/g in mixed medium (Glc and Fru); average: $1.7*10^{11}$ CFU/g.
*Lactobacillus delbrueckii* ssp. *bulgaricus:* $1.0*10^{11}$ CFU/g in glucose medium, $3.0*10^{11}$ CFU/g in mixed medium (Glc and Fru) and $3.0*10^{11}$ CFU/g in fructose medium; average: $2.3*10^{11}$ CFU/g.
*Lactobacillus fermentum:* $3.0*10^{11}$ CFU/g in mixed medium (Glc and Fru) average: $1.7*10^{11}$ CFU/g.

As described above, different amounts of microorganisms (100 mg/L, 10 mg/L and 1 mg/L) were used to determine the residual sugar in the media after 20 h at 37° C. The results are depicted in FIGS. 2A-E. As noted above, *Lactobacillus fermentum* was by far the most effective organism for the conversion of fructose and selectively converted all fructose available in the medium.

Example 3: Comparison of Growth Rates (Optical Density) of the Preferred *L. fermentum* Strains for Use According to the Present Invention in Different Media Comprising Either Glucose, Fructose or Different Mixtures of Fructose and Glucose

*Lactobacillus* minimal media without monosaccharide and low amount of complex sugar was used. Glucose and fructose were added in defined concentrations for sugar metabolism tests separately. Hydrochloric acid (1 M HCl) was added to adjust the pH of the medium to pH 6 at 22° C. MRS media contained 20 g/L dextrose, 10 g/L of pancreatic digest of casein, 10 g/L meat extract, 5 g/L yeast extract, 5 g/L sodium acetate, 2 g/L dipotassium hydrogen phosphate, 2 g/L ammonium citrate, 1 g/L Tween 80, 0.2 g/L magnesium sulfate heptahydrate and 0.05 g/L manganese sulfate heptahydrate. Hydrochloric acid (1 M HCl) was added to adjust the pH of the medium to pH 6 or 8 at 22° C.

*L. fermentum* preparation: Isolation of individual colonies (LB2-7=LF2-7) from pure *L. fermentum* cryogenic cultures on MRS agar plates.

MRS media was inoculated with one *L. fermentum* colony from MRS agar plates. Optical density was measured at 600 nm in a spectrophotometer. Preculture was grown to OD 0.6 and harvested by centrifugation at 3150 rcf for 20 min. Cells were resuspended in 50% glycerol and frozen at −80° C. until use.

Growth of bacteria: Glucose and fructose were filtered sterile and added to minimal media in defined concentrations. *L. fermentum* cells from cryogenic cultures were washed by diluting 50 times in minimal medium, centrifugation at 3150 rcf for 20 min and removing of supernatant. Defined sugar media were inoculated with 1.26E+11 previously washed cells to an initial optical density of 0.06. The different sugar compositions are denoted on the x-axis of FIGS. 3A-F and 4 in g/L. In comparison pure minimal media without sugar was inoculated and used as a blank value to monitor background growth. Cultures were incubated under anaerobic conditions at 37° C. for 24 h. The increase of *L. fermentum* growth was monitored for every hour by spectrometric measurement of optical density (OD) at 600 nm with Tecan infinite M1000. Each sugar culture was determined in quadruplicates for each strain and standard deviation was determined. CFU was calculated by multiplication OD with conversion factor 2.09E+12.

The results demonstrate that all strains grow equally well (OD measurement) and at equal rates in media comprising fructose, glucose or mixtures thereof. The data also show that the strains metabolize fructose and glucose at equally high rates and are therefore suitable for the use according to the present invention. Surprisingly, it was found that strains LF6 (DSM 32737) and LF7 (DSM 32738) preferably grow in fructose-containing media and even show better growth with fructose than with glucose alone (see, e.g., FIG. 4).

Example 4: Comparison of Ethanol Fermentation of the *L. fermentum* Strains for Use According to the Present Invention in Different Media Comprising Either Glucose, Fructose or Different Mixtures of Fructose and Glucose The procedure of sugar utilization was carried out as described in Example 3. Growth of the cultures (LB2-7=LF2-7) in different sugar media (60 g/L glucose, mixture of 30 g/L glucose and 30 g/L fructose, and 60 g/L fructose) was stopped after 5, 7 and 9 hours with centrifugation at 3150 rcf at 4° C. The cell free supernatant was used for the ethanol assay. Ethanol determination (g/L) was carried out according to protocol from the K-ETOH assay kit from Megazyme (Megzyme c.u., Ireland). For the first pretest (FIG. 5A, a first ethanol test was carried out with all strains to decide for best candidates for subsequent analysis. Ethanol production was determined at 60 g/L sugar concentration. The assay was executed with only one sample dilution.) the samples where diluted 1:10 before the assay. For the ethanol assay (FIG. 5B) the samples where diluted 1:5 and 1:50 before the assay. The results are depicted in FIGS. 5A-B.

Example 5: Comparison of Growth of the *L. fermentum* Strains for Use According to the Present Invention in Different pH Environments MRS media (20 g/L dextrose, 10 g/L of pancreatic digest of casein, 10 g/L meat extract, 5 g/L yeast extract, 5 g/L sodium acetate, 2 g/L dipotassium hydrogen phosphate, 2 g/L ammonium citrate, 1 g/L Tween 80, 0.2 g/L magnesium sulfate heptahydrate and 0.05 g/L manganese sulfate heptahydrate) was adjusted to an initial pH of 6.8-8.8 with 1 M KOH. The adjusted media was inoculated with an overnight preculture of the *L. fermentum* strains (LB2-7=LF2-7) for use according to the present invention to OD 0.025. Cultures where incubated at 37° C. OD600 was determined spectrometrically after 1-6, 20 and 24 h. The results are summarized in FIG. 6 (the term "LB" as depicted in FIG. 6 refers to the same strains named "LF").

Example 6: Fructose Depletion Assay for Selected *L. fermentum* Strains for Use According to the Present Invention The procedure of sugar utilization was carried out as described in Example 3 with LF4, LF6 and LF7. Growth of the cultures was stopped after 5, 7 and 9 hours with centrifugation at 3150 rcf at 4° C. The cell free supernatant was used for fructose assay. For analysis the fructose assay kit from BioAssaySys (Bioassay Systems LLC, USA) was used. All strains tested preferred fructose over glucose, as demonstrated in FIG. 7.

The invention claimed is:

1. A method for the therapeutic or prophylactic treatment of hereditary fructose intolerance and/or fructose malabsorption, comprising the steps of:
providing a composition comprising *Lactobacillus fermentum*; and
administering the composition to a subject having hereditary fructose intolerance and/or fructose malabsorption in a pharmaceutically effective amount, wherein the method effectuates the therapeutic or prophylactic treatment of hereditary fructose intolerance and/or fructose malabsorption,
wherein the composition comprises a *Lactobacillus fermentum* selected from the group consisting of LF2 (DSM 32733), LF3 (DSM 32734), LF4 (DSM 32735), LF5 (DSM 32736), LF6 (DSM 32737), and LF7 (DSM 32738).

2. The method according to claim 1, wherein the composition comprises a *Lactobacillus fermentum* selected from the group consisting of LF4 (DSM 32735), LF6 (DSM 32737), and LF7 (DSM 32738).

3. The method according to claim 1, wherein the composition is a human food composition or an animal feed composition.

4. The method according to claim 1, wherein the composition is administered in an amount of about $10^3$-$10^{14}$ CFU *L. fermentum* per day.

5. The method according to claim 1, wherein the composition is administered in an amount of about $10^6$-$10^{13}$ CFU *L. fermentum* per day.

6. The method according to claim 1, wherein the composition is administered in an amount of about $10^8$-$10^{12}$ CFU *L. fermentum* per day.

7. The method according to claim 1, wherein the composition is administered in an amount of about $10^9$-$10^{11}$ CFU *L. fermentum* per day.

8. The method according to claim 2, wherein the composition is a human food composition or an animal feed composition.

9. The method according to claim 1, wherein the composition is administered orally.

10. The method according to claim 2, wherein the composition is administered in an amount of about $10^3$-$10^{14}$ CFU *L. fermentum* per day.

11. The method according to claim 2, wherein the composition is administered in an amount of about $10^6$-$10^{13}$ CFU *L. fermentum* per day.

12. The method according to claim 2, wherein the composition is administered in an amount of about $10^8$-$10^{12}$ CFU *L. fermentum* per day.

13. The method according to claim 2, wherein the composition is administered in an amount of about $10^9$-$10^{11}$ CFU *L. fermentum* per day.

14. The method according to claim 2, wherein the composition is administered orally.

* * * * *